United States Patent [19]

Digenis et al.

[11] 4,115,540

[45] Sep. 19, 1978

[54] RADIODIAGNOSTIC AGENT

[75] Inventors: George A. Digenis; Manvendra B. Shambhu, both of Lexington, Ky.; Michael C. Theodorakis, Gurnee, Ill.

[73] Assignee: The University of Kentucky Research Foundation, Lexington, Ky.

[21] Appl. No.: 696,802

[22] Filed: Jun. 16, 1976

[51] Int. Cl.$^2$ .................... A61K 43/00; A61K 29/00
[52] U.S. Cl. ........................................ 424/1; 23/230.6; 252/301.1 R; 264/0.5; 423/2; 424/1.5; 424/9
[58] Field of Search ................... 424/1, 1.5, 9, 78–80, 424/83; 423/2; 252/301.1 R; 23/230.6; 264/0.5

[56] References Cited

U.S. PATENT DOCUMENTS 4,010,250   3/1977   Parikh et al. ............................ 424/1

Primary Examiner—Benjamin R. Padgett
Assistant Examiner—Christine M. Nucker
Attorney, Agent, or Firm—Birch, Stewart, Kolasch and Birch

[57] ABSTRACT

A radiodiagnostic agent comprising a solid, insoluble nontoxic synthetic resin, such as polystyrene, bearing a detectable amount of technetium 99m thereon. This agent is useful for analyzing the gastrointestinal tract, for example, for gastric emptying time, by means of a gamma camera.

11 Claims, 4 Drawing Figures

RADIODIAGNOSTIC AGENT

This invention relates to a radiodiagnostic agent useful in the clinical analysis of the gastrointestinal tract. More particularly, it relates to a preparation comprising a solid insoluble resin bearing technetium 99m which is especially useful in the evaluation of gastric emptying time.

Various techniques for clinically testing the gastrointestinal tract for numerous ailments are known in the art. Some of these techniques involve the use of radioactivity as a means of scanning the G.I. tract. In this regard, technetium 99m is the most commonly used radionuclide in nuclear medicine because of its favorable imaging characteristics (gamma energy 140 KeV, half-life 6.0 hours).

Chemically, technetium (Tc) belongs to Group VII B of the Periodic Table (along with manganese and rhenium) and is known to exist in valence states ranging from +1 to +7. The stable forms of the metal in water are the pertechnetate ($TcO_4^-$, similar to $MnO_4^-$) and $TcO_2$. Technetium 99m is formed by the beta decay of molybdenum 99 and decays to Tc 99 according to the following equation:

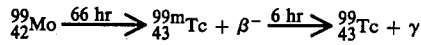

$$^{99}_{42}Mo \xrightarrow{66\ hr} {}^{99m}_{43}Tc + \beta^- \xrightarrow{6\ hr} {}^{99}_{43}Tc + \gamma$$

Tc 99m is obtained in the pertechnetate form by elution with normal saline from a technetium generator ("Chemistry of Technetium 99m", J. Steigman and P. Richards, "Seminars in Nuclear Medicine", 4, 269 (1974)).

One of the specific techniques for clinically evaluating gastric emptying time in patients having abnormalities of gastric function comprises administering a pertechnetate solution to the patient together with a meal and monitoring its passage through the gastrointestinal tract by means of a gamma camera. However, this technique using an aqueous solution of Tc 99m has two drawbacks. First, the radioisotope is absorbed from the G.I. tract, thereby making the test unreliable, and, secondly, the solution does not move at the same rate as the solid food particles.

To overcome these difficulties, a sulfur colloid of technetium has been employed in the place of the pertechnetate solution ("The Gamma Camera in Clinical Evaluation of Gastric Emptying", A. P. van Dam, Radiology, 110, 155 (1974)). However, this colloidal preparation is generally unstable and is difficult to prepare.

Therefore, there has been a great need in this field for a simple preparation which can be used on the clinical level even by relatively inexperienced personnel and which gives reliable results quickly and effectively without any ancillary problems.

Accordingly, one of the objects of the present invention is to provide a radiodiagnostic agent which can be readily and simply prepared for use in clinical evaluations and which overcomes the disadvantages and deficiencies of the prior art as noted above.

Another object of the invention is to provide a radiodiagnostic agent having a high retention of label and which is clinically stable for use in determining gastric emptying time reliably and effectively.

These and other objects and advantages of the invention will become apparent to those skilled in the art from a consideration of the following specification and claims, taken in conjunction with the accompanying drawings, which show various properties of the diagnostic preparation of the invention.

In accordance with the present invention, it has been found that a preparation comprising a solid, insoluble non-toxic synthetic resin bearing technetium 99m provides a new and useful radiodiagnostic agent which is particularly well suited for the clinical evaluation of gastric emptying time. The technetium 99m-containing resin has been found to be a preparation from which little if any radioisotope is lost upon suspending the resin in aqueous buffers and gastric and intestinal fluids. Thus, this solid form of technetium 99m comprises a convenient preparation which can be readily imaged externally by the use of a gamma camera. Accordingly, in addition to use in the clinical evaluation of gastric emptying time, the Tc-99m bearing resin of the invention can be used, for example, in in vivo studies on the disintegration of various pharmaceutical dosage forms such as pills or capsules when incorporated therein in the solid dose form.

The solid preparation of technetium 99m of the invention is obtained by binding or chelating the isotope to an insoluble, non-toxic chemically inert synthetic resin. This solid preparation is stable and is very simple to prepare, for example, within thirty minutes or less. Very little radionuclide is absorbed into the blood stream upon administration because of its physical nature. For example, less than 1%, which is almost negligible, of the radionuclide was detected in an experimental animal (dog) when administered thereto orally. Moreover, the preparation of the invention, being in a granular form, can be easily handled and readily mixed with solid food. Thus, it meets all of the criteria of a safe and reliable diagnostic agent which can be used clinically in the field of nuclear medicine.

The base resin employed is preferably a porous non-toxic synthetic resin such as "popcorn" polystyrene, which is a white, brittle, insoluble and highly porous resin of irregular shape. Other forms of polystyrene can be suitably employed. These include polystyrene prepared by bulk, suspension, solution or emulsion polymerization. Copolymers of styrene with suitable copolymerizable monomers may also be employed. Other polymers that can be prepared in granular form and which can bear the polyamine functions discussed below can also be used advantageously in the diagnostic preparation of the invention.

Chloromethyl ($CH_2Cl$) groups or similar chemical binding functions are introduced into the base polymer. These functions are then converted to aliphatic polyamines by reaction with various amines, such as those shown in Table 1 below. The resulting resin is then treated with a solution of sodium pertechnetate, favorably at pH 1.5, resulting in the transfer of the technetium from the solution to the resin. The resulting Tc-bearing resin is then washed with water until the washings do not show any radioactivity.

The reaction scheme employed to prepare a polystyrene resin bearing Tc 99m is thus as follows:

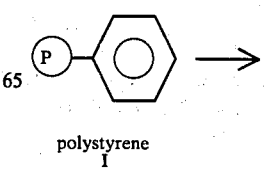

polystyrene
I

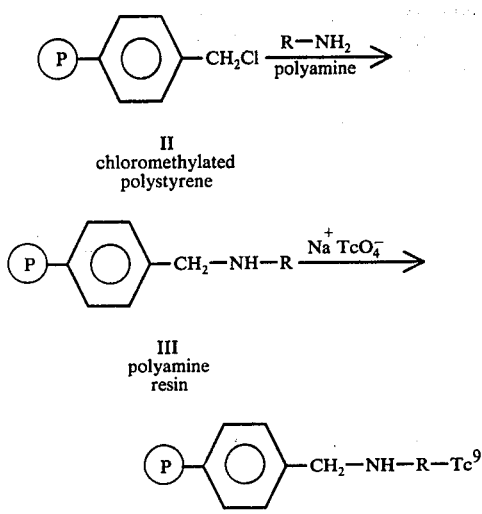

II
chloromethylated polystyrene

III
polyamine resin

TABLE 1

Properties of the resins (III) obtained by reacting chloromethylated polystyrene (II, % Cl=13.2) with various polyamines

| Resin No. | Polyamine | Analysis of the product III | |
|---|---|---|---|
| | | % Cl | % N |
| IIIa | ethylenediamine ("en" or EDA) | 0.07 | 6.46 |
| IIIb | diethylenetriamine ("dien" or DTA) | 0.11 | 8.1 |
| IIIc | triethylenetetramine ("trien" or TETA) | 0.08 | 9.02 |
| IIId | pentaethylenetetramine ("tetren" or PETA) | 0.66 | 8.45 |

The general technique for the synthesis of polystyrene with various functions and immobilization with substances such as amino acids on the polymer is known in the art; for example, note Merrifield, *J. Amer. Chem. Soc.*, 85, 2149 (1963) and Letsinger, *J. Amer. Chem. Soc.*, 85, 3046 (1963). However, the novel finding of the invention is the binding of Tc 99m thereon and the use of the resulting preparation in clinical evaluations.

The following Example is given merely as illustrative of the present invention and is not to be considered as limiting.

EXAMPLE

Figure 1:
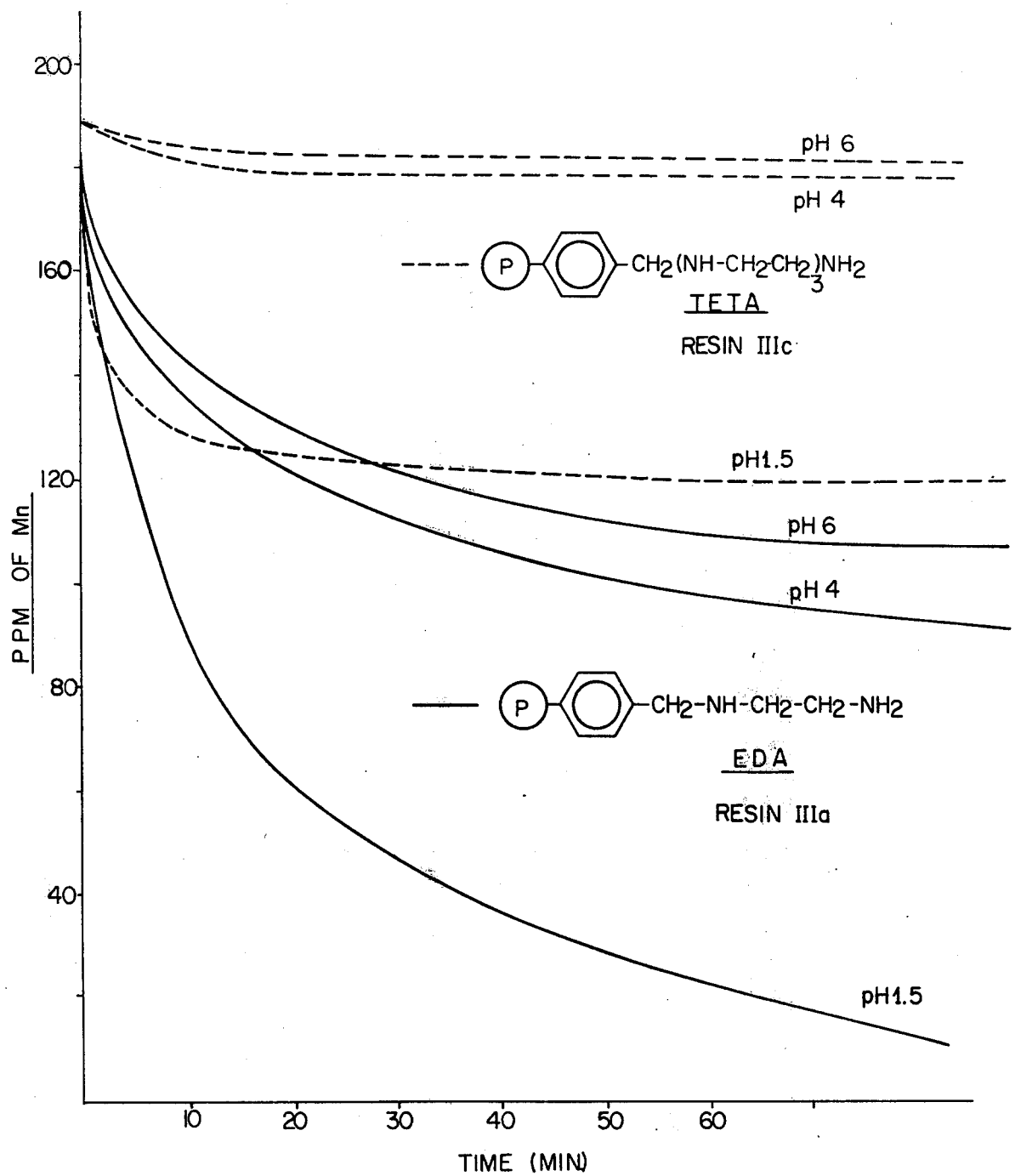
FIG. 1 represents the uptake of KMn O₄ by Polystyrene-Polyamine resins.

Preparation of "popcorn" polystyrene (I) — The polymer is prepared by copolymerization of styrene with a small amount of divinylbenzene (0.2 per cent). The polymerization is carried out at 55° C. in the absence of air after the addition of a few seeds of the polymer and usually requires about 48 hours. After washing with organic solvents, the resin is dried and reduced to 40-100 mesh size.

Preparation of chloromethylated polystyrene (II) — To a suspension of polystyrene (70.0 g) in 500 ml chloroform at 0° C., a solution of anhydrous stannic chloride (35 ml) in chloromethylmethyl ether (90 ml) is added over 30 minutes. The mixture is stirred at room temperature for 2 hours and filtered. The polymer is washed repeatedly with chloroform, dioxane-water, water and finally methanol. After drying at 60° C. under vacuo, the polymer (85 g) is found to contain 3.5 meq of chlorine per gram.

Preparation of the polyamine resins (III) — Four polyamines are immobilized on the resin (see Table 1) by the following procedure: The chloromethylated resin beads (II, 10 g) are swelled in 40 ml pyridine and 20 ml of the polyamine is added. The mixture is heated over a boiling water bath for 12 hours or until the analysis of the washed resin shows little unreacted chlorine (below 0.5 per cent). The resin is separated by filtration and washed repeatedly with hot pyridine, water and methanol.

To demonstrate the abilities of the polyamine resins (III) to reduce metals in a high oxidation state (+7) to a lower state before immobilization of the metal to the polymer matrix, the resins are treated with potassium permanganate solutions at various pH values. (Manganese and technetium both belong to Group VII B in the Periodic Table. Pertechnetate and permanganate anions are known to be similar in many respects.) The resin is added to the permanganate solution which is decolorized due to the reducing ability of the resin. Samples are taken periodically from the solution and analyzed for manganese. The results are shown in FIG. 1 in the accompanying drawings.

Figure 2:
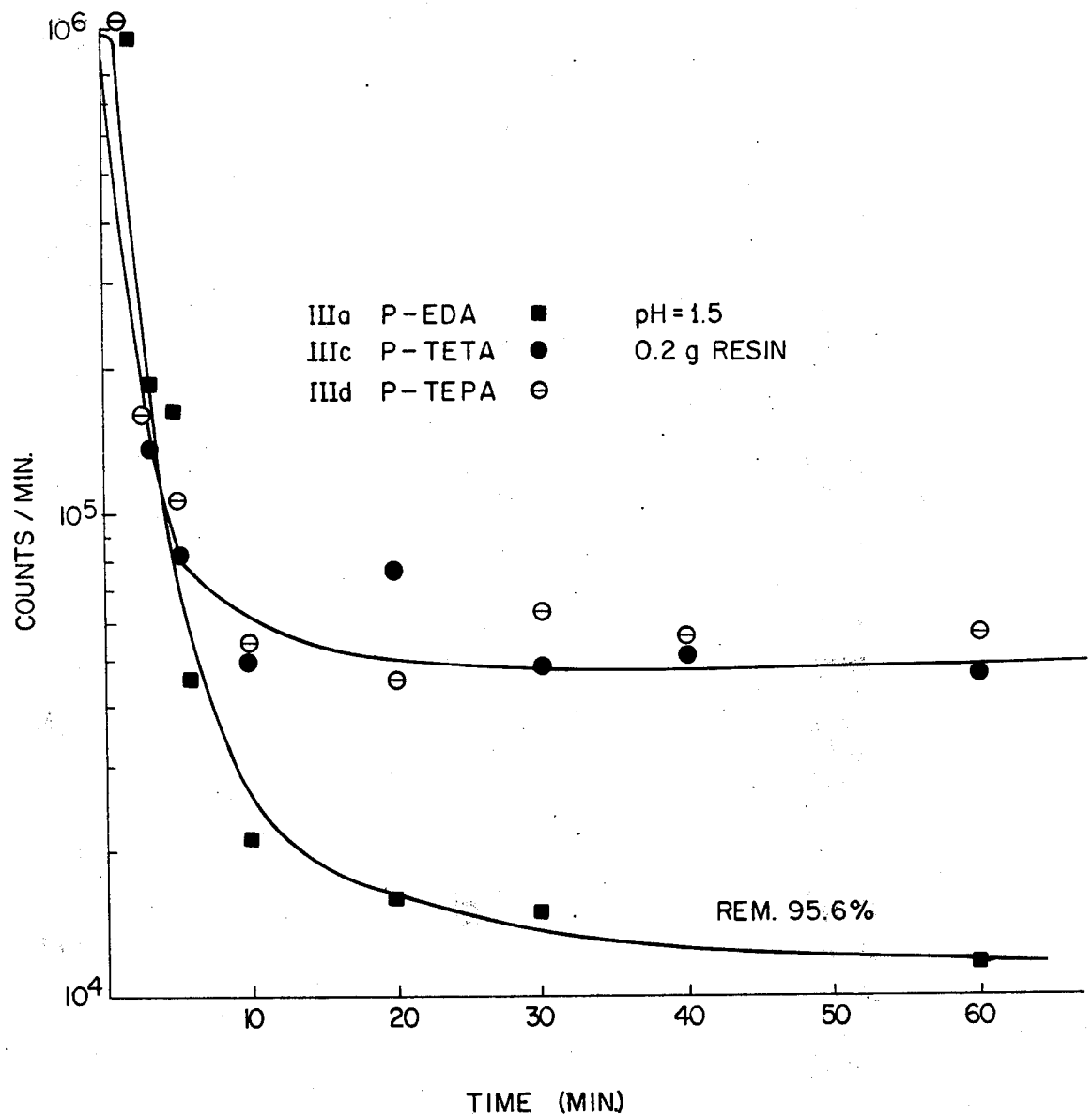
FIG. 2 represents the uptake of $^{99}$Tc O$^-_4$ by Polystyrene-Polyamine resin.

The technetium bearing resins can be prepared as follows: The polyamine resin is suspended in an aqueous solution at pH 1.5 obtained by the addition of dilute hydrochloric acid. The required amount of the sodium pertechnetate solution is added and the mixture stirred for 30 minutes. Samples are taken from the solution periodically and analyzed for technetium by counting. The results are shown in FIG. 2 in the drawings for two resins (IIIa and IIIc). The resin is removed by filtration after 30 minutes and washed three times with water. The resin can then be mixed with food for gastric emptying studies. For applications requiring dry resin, it can be washed with a low boiling organic solvent such as acetone and dried.

Figure 3:
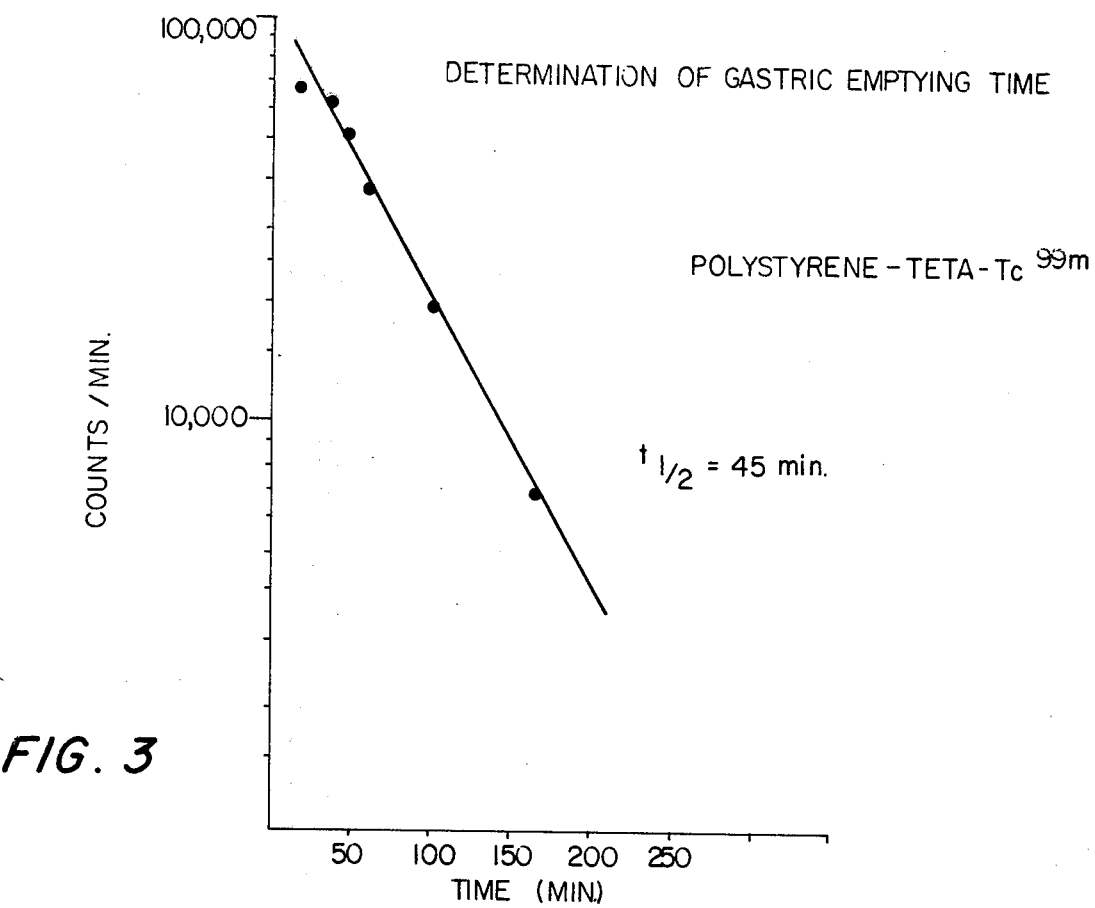
FIGS. 3 and 4 represent a determination of gastric emptying time.

In a typical experiment, 0.5 g of the resin is treated with 100 ml of a solution of sodium pertechnetate containing the Tc-99m as pertechnetate. The results of the gastric emptying studies on a human volunteer are shown in FIG. 3 in the drawings. The logarithm of the counts is plotted as a function of time (minutes).

Figure 4:
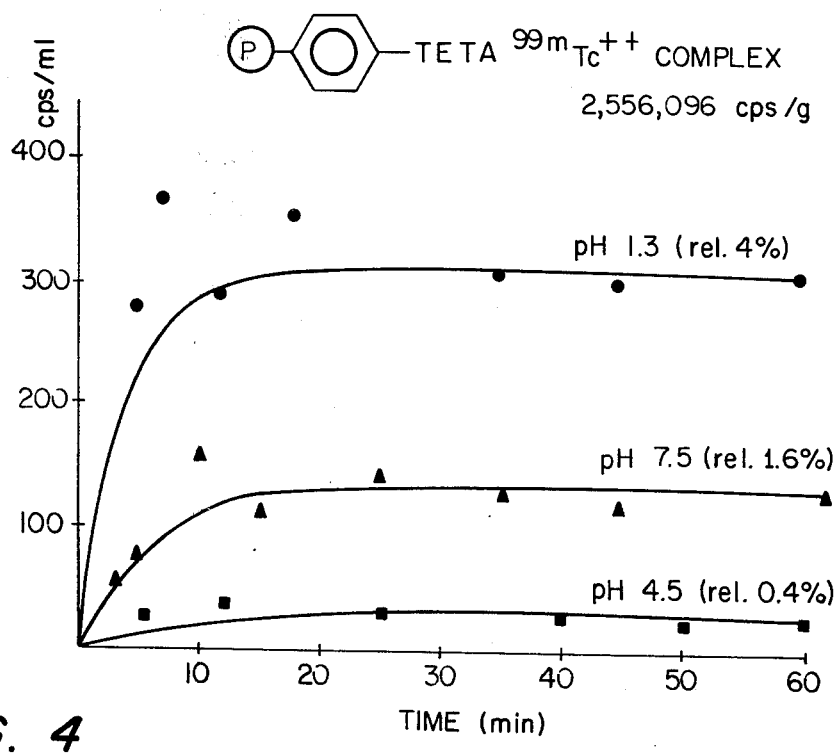

FIG. 4 illustrates a test conducted to show that very little activity is lost with the preparation of the invention even in strongly acidic conditions. For instance, only about 4% activity was released initially when the preparation was washed at pH 1.3, and even this loss in activity stopped after about 15 minutes in this strongly acidic solution. Lower release percentages are observed as the pH approaches neutrality. Thus, it is quite clear that the labeled polymer complex of the invention is highly stable under the conditions as are found with gastric contents.

The radiodiagnostic agent of the invention has been tested both in dogs as well as humans for the evaluation of gastric emptying, as noted above. Generally, disappearance half times (human) of 40 minutes to 150 minutes have been observed.

Hence, the present invention provides an insoluble resin-polyamine-Tc 99m complex which is stable, easy to prepare and gives reliable results when used clinically as a diagnostic agent.

The invention being thus described, it will be obvious that the same may be varied in many ways. Such variations are not to be regarded as a departure from the spirit and scope of the invention, and all such modifications are intended to be included within the scope of the following claims.

We claim:

1. A method for analyzing the gastrointestinal tract of a human being or animal which comprises orally administering a diagnostic amount of a solid, insoluble non-toxic synthetic resin bearing a detectable amount of Tc 99m thereon, and analyzing the number of radioactive counts given off by the decay of the Tc 99m as said resin passes through the gastrointestinal tract.

2. A non-biodegradable radiodiagnostic agent useful for analyzing the gastrointestinal tract which comprises a solid, insoluble, non-toxic synthetic resin bearing a detectable amount of Tc-99m therein, said agent having no appreciable loss of Tc-99m to the digestive system.

3. The non-biodegradable radiodiagnostic agent of claim 2, wherein the synthetic resin is polystyrene containing an aliphatic polyamine to which the Tc-99m is chemically bound.

4. The non-biodegradable radiodiagnostic agent of claim 2, wherein said aliphatic polyamine is ethylenediamine, diethylenetriamine, triethylenetetramine or pentaethylenetetramine.

5. The non-biodegradable radiodiagnostic agent of claim 2, wherein the synthetic resin is a polyacrylate containing COOH, OH, or $NH_2$ functions for chemically bonding the Tc-99m thereto.

6. The non-biodegradable radiodiagnostic agent of claim 5, wherein the polyacrylate is hydroxymethylmethacrylate polymer.

7. The non-biodegradable radiodiagnostic agent of claim 2, wherein the synthetic resin is chemically bound to Tc-99 m by a member selected from the group consisting of diethylenetriaminepentacetic acid (DTPA), iminodiacetic acid, and $\beta$-diketones.

8. A process for the preparation of a radiodiagnostic agent which comprises adding phosgene to hydroxymethylmethacrylate polymer followed by the addition of a polyamine and then adding an aqueous solution of sodium pertechnetate thereto, thereby forming a polyamine-Tc-99m complex-containing polyhydroxymethylmethacrylate resin.

9. A process for the preparation of a radiodiagnostic agent which comprises mixing chloromethylated polystyrene with an organic swelling agent and then further adding an aliphatic polyamine thereto, heating the mixture until a polyamine-containing resin is obtained, suspending said polyamine-containing resin in an aqueous acidic solution, and then adding an aqueous solution of sodium pertechnetate thereto, thereby forming a polyamine-Tc 99m complex-containing polystyrene resin.

10. The process of claim 9, wherein said aliphatic polyamine is ethylenediamine, diethylenetriamine, triethylenetetramine or pentaethylenetetramine.

11. The process of claim 10, wherein said organic swelling agent is pyridine.

* * * * *